(12) United States Patent
Funada et al.

(10) Patent No.: US 11,155,848 B2
(45) Date of Patent: Oct. 26, 2021

(54) METHOD OF PRODUCING SUGAR LIQUID

(71) Applicant: Toray Industries, Inc., Tokyo (JP)

(72) Inventors: Shigeyuki Funada, Kamakura (JP); Hiroyuki Kurihara, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 15/108,431

(22) PCT Filed: Dec. 26, 2014

(86) PCT No.: PCT/JP2014/084476
§ 371 (c)(1),
(2) Date: Jun. 27, 2016

(87) PCT Pub. No.: WO2015/099109
PCT Pub. Date: Jul. 2, 2015

(65) Prior Publication Data
US 2016/0326559 A1    Nov. 10, 2016

(30) Foreign Application Priority Data
Dec. 27, 2013 (JP) .............................. JP2013-271600

(51) Int. Cl.
*C12P 19/14* (2006.01)
*C12P 19/02* (2006.01)

(52) U.S. Cl.
CPC ............... *C12P 19/14* (2013.01); *C12P 19/02* (2013.01)

(58) Field of Classification Search
None
See application file for complete search history.

(56) References Cited

U.S. PATENT DOCUMENTS

| | | | |
|---|---|---|---|
| 8,822,201 B2 | 9/2014 | Kohler et al. | |
| 9,624,516 B2 | 4/2017 | Kurihara et al. | |
| 2009/0042266 A1 | 2/2009 | Vehmaanpera et al. | |
| 2011/0312043 A1* | 12/2011 | Burlew | B01D 3/002 435/129 |
| 2013/0059345 A1* | 3/2013 | Kurihara | C12P 19/14 435/99 |

FOREIGN PATENT DOCUMENTS

| | | |
|---|---|---|
| CN | 101899488 A | 12/2010 |
| CN | 102791874 A | 11/2012 |
| CN | 102978125 A | 3/2013 |
| EP | 2 256 208 | 12/2010 |
| EP | 2 548 966 | 1/2013 |
| JP | 55-029951 A | 3/1980 |
| JP | 63-087994 A | 4/1988 |
| JP | 3041380 B2 | 3/2000 |
| JP | 2001-095597 A | 4/2001 |
| JP | 2006-087319 A | 4/2006 |
| JP | WO 2011115039 A1 * | 9/2011 ............. C12P 19/14 |
| WO | 2008/112729 A2 | 9/2008 |
| WO | 2012/133495 A1 | 10/2012 |
| WO | 2013/016115 | 1/2013 |

OTHER PUBLICATIONS

Ali L. Sidi et al., "Enzymatic Hydrolysis of Sugar Beet Pulp," Biotechnology Letters, vol. 6, No. 11, 1984, pp. 723-728.
G. Beldman et al., "Application of Cellulose and Pectinase from Fungal Origin for the Liquefaction and Saccharification of Biomass," Enzyme Microb. Technol., vol. 6, Nov. 1984, pp. 503-507.
A. Aden et al., "Lignocellulosic Biomass to Ethanol Process Design and Economics Utilizing Co-Current Dilute Acid Prehydrolysis and Enzymatic Hydrolysis for Corn Stover," NREL Technical Report, Jun. 2002 (154 pages).
Watanabe, E., "Membrane Separation in Cellulose Saccharification and Mixed Enzyme Culture Liquid Recycling," *Medicine and Biology*, 1989, vol. 119, No. 3, pp. 131-135 with English translation.
Okado, N., "Pectinase o Riyo shita Yasai Kajitsu Shokuhin no Kaihatsu," *Food Chemicals*, vol. 19, No. 9, 2003, pp. 72-75 with partial English translation.
Supplementary European Search Report dated Jul. 11, 2017, of corresponding European Application No. 14874849.4.
Sun, Y., et al., "Hydrolysis of lignocellulosic materials for ethanol production: a review," *Bioresource Technology*, vol. 83, No. 1, May 2002, pp. 1-11.
The First Office Action dated Aug. 16, 2018, of counterpart Chinese Application No. 201480063493.1, along with an English translation.
Office Action dated Nov. 27, 2018, of counterpart Japanese Application No. 2015-501982, along with an English translation.
Office Action dated Dec. 20, 2019, of counterpart Malaysian Application No. PI2016702364.
Communication of Further Notices of Opposition dated Feb. 12, 2021, of counterpart European Application No. 14874849.4.
Communication of a Notice of Opposition dated Feb. 4, 2021, of counterpart European Application No. 14874849.4.
Bhale, U.N. et al., "Enzymatic activity of Trichoderma species," Novus Natural Science Research, Apr. 11, 2012, vol. 1, No. 4, Abstract only.
Mehta, Aksh ta et al., "Fungal lipases: a review," *Journal of Biotech Research*, Nov. 2017, vol. 8; pp. 58-77, Abstract only.
"Cellulase from *Trichoderma* sp.," SigmaAldrich.com, 00615, Accessed Jan. 15, 2021, Screenshot retrieved at www.sigmaaldrich.com/catalog/product/sigma/c0615.
Brijwani, Khushal et al., "Production of a cellulolytic enzyme system in mixed-culture solid-state fermentation of soybean hulls supplemented with wheat bran," *Process Biochemistry*, Aug. 27, 2009, vol. 45, pp. 120-128, Abstract only.

(Continued)

*Primary Examiner* — Paul J Holland
(74) *Attorney, Agent, or Firm* — DLA Piper LLP (US)

(57) ABSTRACT

A method of producing a sugar liquid from cellulose-containing biomass includes step (1) of hydrolyzing cellulose-containing biomass by a filamentous fungus-derived cellulase; and step (2) of filtering a hydrolysate obtained in step (1) through an ultrafiltration membrane to recover the filamentous fungus-derived cellulase as a non-permeate and to obtain a sugar liquid as a permeate, wherein the cellulose-containing biomass is treated with one or more enzymes selected from the group consisting of pectinase, glucoamylase, and lipase at a stage previous to step (1) or in step (1).

5 Claims, No Drawings

(56) References Cited

OTHER PUBLICATIONS

Monsoor, M.A. et al., "Preparation and Functional Properties of Soy Hull Pectin," *Journal of the American Oil Chemists' Soceity*, Jul. 2001, Paper No. J9872, vol. 78, No. 7, pp. 709-713, Abstract only.

Babu, Chalamacharla et al., "Wheat Bran-Composition and Nutritional Quality: A Review " *Advances in Biotechnology & Microbiology*, Apr. 30, 2018, vol. 9, pp. 21-27, Abstract only.

Rajesh, E.M. et al., "Investigation of lipase production by *Trichoderma reesei* and optimization of production parameters," *Electronic Journal of Environmental, Agricultural and Food Chemistry*, Jan. 2010, vol. 9, No. 7, pp. 1177-1189, Abstract only.

Adams, P.R., "Growth and amylase production of *Thermoascus aurantiacus* Miehe," Biotechnology and Applied Chemistry, 1992, vol. 15, No. 3, pp. 311-313, Abstract only.

Martins, E. et al., "Solid state production of thermostable pectinases from thermophilic *Thermoascus aurantiacus*," Process Biochemistry, Apr. 2002, vol. 37, Issue 9, pp. 949-954, Abstract only.

* cited by examiner

METHOD OF PRODUCING SUGAR LIQUID

TECHNICAL FIELD

This disclosure relates to methods of producing a sugar liquid which is usable, for example, in a fermentation raw material from cellulose-containing biomass.

BACKGROUND

Fermentative production processes for chemical substances using a sugar as a raw material are utilized in the production of various industrial raw materials. As sugars serving as raw materials for fermentation, those derived from edible raw materials such as sugar cane, starch, and sugar beet are industrially utilized at present. However, in view of rise in prices of edible raw materials due to the increase in world population in the future or from the ethical aspect of competition with edible use, the construction of processes to effectively produce a sugar liquid from a renewable non-edible resource, i.e., cellulose-containing biomass or processes to effectively convert the resultant sugar liquid into an industrial raw material as a fermentation raw material is a future task.

A known method of producing a sugar liquid from cellulose-containing biomass is a method of producing a sugar liquid through hydrolysis of cellulose-containing biomass by a dilute sulfuric acid followed by a further enzymatic treatment with cellulase or the like (A. Aden et al., "Lignocellulosic Biomass to Ethanol Process Design and Economics Utilizing Co-Current Dilute Acid Prehydrolysis and Enzymatic Hydrolysis for Corn Stover," NREL Technical Report (2002)), in addition to the method of producing a sugar liquid through acid hydrolysis of cellulose and hemicellulose by a commonly-known concentrated sulfuric acid. As methods without using an acid, disclosed are a method of producing a sugar liquid through a subcritical water treatment of cellulose-containing biomass at about 250 to 500° C. followed by a further saccharification enzymatic treatment (Japanese Patent Application Laid-Open Publication No. 2001-95597); and a method of producing a sugar liquid through hydrolysis of cellulose-containing biomass by pressurized hot water of 240 to 280° C. followed by a further saccharification enzymatic treatment (Japanese Patent No. 3041380). Among these methods, there have been widely studied methods of hydrolyzing biomass especially by using a saccharification enzyme providing less energy consumption and less environmental impact, as well as more sugar yield. Such methods with a saccharification enzyme, however, involve drawbacks such as expensiveness of enzyme.

To solve the above-mentioned technological problem involved in the methods of sugar liquid production through a saccharification enzyme treatment, methods of recovering to reuse the saccharification enzyme used in the hydrolysis have been suggested. For example, a method comprises carrying out continuous solid-liquid separation by a spin filter and filtering the resultant sugar liquid through an ultrafiltration membrane to recover an enzyme (Japanese Patent Application Laid-Open Publication No. 2006-87319); and a method comprising inputting a surfactant at an enzymatic saccharification stage to inhibit the enzyme adsorption, thereby improving the recovery efficiency (Japanese Patent Application Laid-Open Publication No. S63-87994).

Methods of hydrolyzing cellulose-containing biomass by using a saccharification enzyme have been developed as described above, but are still unsatisfactorily effective from the viewpoint of reducing the saccharification enzyme consumption. Thus, it could be helpful to develop sugar liquid production processes capable of more effectively reducing the saccharification enzyme consumption in the hydrolysis of cellulose-containing biomass than conventional methods.

SUMMARY

We thus provide:

[1] A method of producing a sugar liquid from cellulose-containing biomass, comprising:
  step (1) of hydrolyzing cellulose-containing biomass by a filamentous fungus-derived cellulase; and
  step (2) of filtering a hydrolysate obtained in the step (1) through an ultrafiltration membrane to recover the filamentous fungus-derived cellulase as a non-permeate and to obtain a sugar liquid as a permeate,
wherein the cellulose-containing biomass is treated with one or more enzymes selected from the group consisting of pectinase, glucoamylase, and lipase at a stage previous to the step (1) or in the step (1).

[2] The method of producing a sugar liquid according to [1], wherein the cellulose-containing biomass is one or more biomasses selected from the group consisting of grain hull biomass, straw, and bagasse.

[3] The method of producing a sugar liquid according to [2], wherein the grain hull biomass is one or more biomasses selected from the group consisting of a corn hull, a soybean hull, and a wheat hull.

[4] The method of producing a sugar liquid according to any one of [1] to [3], wherein the weight of the one or more enzymes selected from the group consisting of pectinase, glucoamylase, and lipase is $1/10$ or less based on the weight of the filamentous fungus-derived cellulase.

[5] The method of producing a sugar liquid according to any one of [1] to [4], wherein the cellulose-containing biomass is treated with the three enzymes, pectinase, glucoamylase, and lipase at the stage previous to the step (1) or in the step (1).

[6] The method of producing a sugar liquid according to any one of [1] to [5], wherein the step (2) is a step of filtering, through an ultrafiltration membrane, a solution component obtained by subjecting the hydrolysate obtained in the step (1) to solid-liquid separation.

[7] The method of producing a sugar liquid according to [6], wherein the solid-liquid separation is carried out by press filtration.

It is possible to improve the amount of the saccharification enzyme to be recovered from the sugar liquid production steps using the cellulose-containing biomass as a raw material.

DETAILED DESCRIPTION

Each of the steps of our methods will be individually described below.

Step (1)

Step (1) is hydrolyzing cellulose-containing biomass by a filamentous fungus-derived cellulase.

The cellulose-containing biomass used in step (1) refers to bioresources containing at least cellulose. Specific examples of the cellulose-containing biomass include herbaceous biomass such as bagasse, switchgrass, napier grass, Erianthus, corn stover or straw (rice straw, wheat/barley straw); woody biomass such as trees and shrubs or waste building material;

biomass derived from aquatic environment such as algae or seagrass; and grain hull biomass such as corn hulls, wheat hulls, soybean hulls or rice hulls. Grain hull biomass, straw, and bagasse are most effective and preferably utilized.

The hydrolysis of cellulose-containing biomass is intended to reduce the molecular weight of cellulose to generate monosaccharides or oligosaccharides. In the hydrolysis of cellulose-containing biomass, a hemicellulose component such as xylan, mannan or arabinan is also hydrolyzed simultaneously. In this step, a filamentous fungus-derived cellulase is used as a saccharide enzyme for hydrolysis of cellulose-containing biomass.

The filamentous fungus-derived cellulase is an enzyme composition having an activity of hydrolyzing cellulose for saccharification and contains a plurality of enzyme components such as cellobiohydrolase, endoglucanase, exoglucanase, β-glucosidase, xylanase, and xylosidase. The filamentous fungus-derived cellulase can carry out efficient hydrolysis of cellulose through the concert effects or complementary effects of the plurality of enzyme components in the breakdown of cellulose.

Examples of the cellulase derived from a filamentous fungus, the genus *Trichoderma*, the genus *Aspergillus*, the genus *Cellulomonas*, the genus *Chlostridium*, the genus *Streptomyces*, the genus *Humicola*, the genus *Acremonium*, the genus *Irpex*, the genus *Mucor*, the genus *Talaromyces*, the genus *Phanerochaete*, white-rot fungi, and brown-rot fungi. Among these filamentous fungus-derived cellulases, the genus *Trichoderma*-derived cellulase having a high cellulose breakdown activity is preferably used.

The genus *Trichoderma*-derived cellulase is an enzyme composition containing cellulase derived from microorganisms of the genus *Trichoderma* as a major component. The microorganisms of the genus *Trichoderma* are not particularly restricted, and are preferably *Trichoderma reesei*; and specific examples thereof can include *Trichoderma reesei* QM9414, *Trichoderma reesei* QM9123, *Trichoderma reesei* RutC-30, *Trichoderma reesei* PC3-7, *Trichoderma reesei* CL-847, *Trichoderma reesei* MCG77, *Trichoderma reesei* MCG80, and *Trichoderma viride* QM9123. Mutant strains with improved productivity of cellulase by subjecting the above-mentioned microorganisms derived from the genus *Trichoderma* to mutagenesis using a mutagen, UV irradiation, or the like may be used.

Cellobiohydrolase is a general term for enzymes characterized by hydrolyzing cellulose, in the unit of cellobiose, from the terminal portion thereof, and the following two types are known: Cellobiohydrolase I which initiates cleavage from the reducing terminal side of the cellulose chain and Cellobiohydrolase II which does from the non-reducing terminal side. The group of enzymes belonging to cellobiohydrolase is described as the EC number: EC3.2.1.91.

Endoglucanase is a general term for enzymes characterized by randomly hydrolyzing cellulose from the central portion of a cellulose molecular chain. The group of enzymes belonging to endoglucanase is described as the EC number: EC3.2.1.4, EC3.2.1.6, EC3.2.1.39 or EC3.2.1.73.

Exoglucanase is a general term for enzymes characterized by randomly hydrolyzing cellulose from the terminal end of a cellulose molecular chain. The group of enzymes belonging to exoglucanase is described as the EC number: EC3.2.1.7 or EC3.2.1.58.

β-glucosidase is a general term for enzymes characterized by acting on cello oligosaccharides or cellobiose. The group of enzymes belonging to 3-glucosidase is described as the EC number: EC3.2.1.21.

Xylanase is a general term for enzymes characterized by acting on hemicellulose or, in particular, xylan. The group of enzymes belonging to xylanase is described as EC number: EC3.2.1.8.

Xylosidase is a general term for enzymes characterized by acting on xylooligosaccharides. The group of enzymes belonging to xylosidase is described as EC number: EC3.2.1.37.

Crude enzymes are preferably used as the filamentous fungus-derived cellulase. The crude enzyme is derived from the culture supernatant of the medium in which the microorganism is cultured for any period of time, the medium being prepared such that the filamentous fungus produces cellulase. Medium components used are not particularly restricted; and a medium with cellulose being added can be generally used to promote the production of cellulase. Then, as the crude enzyme, a culture liquid as is or the supernatant of the culture obtained only by removing the fungus body is preferably used.

A weight ratio of each enzyme component in the crude enzyme is not particularly restricted. For example, a culture liquid derived from *Trichoderma reesei* contains 50 to 95% by weight cellobiohydrolase; and the remaining components include endoglucanase, β-glucosidase, and the like. The genus *Trichoderma* microorganisms produce strong cellulase components in a culture liquid. On the other hand, with regard to β-glucosidase, the enzyme is kept inside the cell or on the surface layers of the cell, and therefore the β-glucosidase activity is low in the culture liquid. In view this, β-glucosidase from different species or the same species may be further added to the crude enzyme. As the β-glucosidase from different species, β-glucosidase derived from the genus *Aspergillus* can be preferably used. Examples of the β-glucosidase derived from the genus *Aspergillus* include Novozyme 188 which is commercially available from Novozymes A/S. β-glucosidase from different species or the same species may be added to the crude enzyme by a method comprising introducing a gene to the genus *Trichoderma* microorganism, culturing the genus *Trichoderma* microorganism that is genetically-modified to produce the gene product in a culture liquid, and isolating the culture liquid.

The cellulose-containing biomass is preferably pretreated to improve hydrolysis efficiency prior to hydrolysis thereof by filamentous fungus-derived cellulase. A method of pretreating the cellulose-containing biomass is not particularly restricted and specific examples thereof include an acid treatment, a sulfuric acid treatment, a dilute sulfuric acid treatment, an alkali treatment, a sodium hydroxide treatment, an ammonia treatment, a hydrothermal treatment, a subcritical water treatment, a pulverizing treatment, and a steaming treatment. A hydrothermal treatment and a dilute sulfuric acid treatment are preferred.

A hydrothermal treatment is carried out at a temperature of 100 to 400° C. for 1 second to 60 minutes after addition of water so that the solid concentration of biomass arrives at 0.1 to 50% by weight. The treatment under such a temperature condition causes hydrolysis of cellulose or hemicellulose. Particularly, a temperature of 100 to 250° C. is preferred; and a period of time for the treatment of 5 to 30 minutes is preferred. The number of times of the treatment is not particularly restricted. It is enough to carry out the treatment at least once. Particularly when the treatment is carried out twice or more, the first treatment and the second and subsequent treatments may be carried out under different conditions.

In the hydrothermal treatment, sulfuric acid may be added for a dilute sulfuric acid treatment. The amount of sulfuric acid to be added is preferably 0.1 to 150 mg per g (weight) of cellulose-containing biomass.

The conditions for a hydrolysis reaction by a filamentous fungus-derived cellulase are not restricted as long as hydrolysis is carried out in accordance with reaction conditions preferred for the filamentous fungus-derived cellulase. When filamentous fungus-derived cellulase is used, a general reaction temperature is preferably 15 to 100° C., more preferably 40 to 60° C. and still more preferably 50° C. The pH of hydrolysis is preferably pH 3 to 9, more preferably pH 4 to 5.5 and still more preferably 5. The pH can be adjusted by addition of an acid or an alkali to attain the desired pH and a buffer may be used as appropriate. In addition, to promote contact between the cellulose-containing biomass and the saccharification enzyme and make the sugar concentration of the hydrolysate uniform, mixing with stirring is preferably carried out. Water is added so that the solid concentration of cellulose falls preferably 1 to 25% by weight and more preferably 5 to 20% by weight.

Step (2)

Step (2) involves filtering a hydrolysate obtained in step (1) through an ultrafiltration membrane to recover the filamentous fungus-derived cellulase as a non-permeate and to obtain a sugar liquid as a permeate. The enzyme recovered as the non-permeate can be reused in step (1); and the enzyme consumption in step (1) can be reduced.

The molecular weight cut off of the ultrafiltration membrane is not particularly restricted as long as it allows passage of at least monosaccharides, i.e., glucose (molecular weight 180) and xylose (molecular weight 150) and can block the filamentous fungus-derived cellulase. It is preferred to be a molecular weight cut off of 500 to 50,000. From the viewpoint of separating foreign substances exhibiting actions inhibitory to the enzymatic reaction from the enzyme, the molecular weight cut off is more preferably 5,000 to 50,000 and still more preferably 10,000 to 30,000.

As materials of the ultrafiltration membrane, polyether sulfone (PES), polysulfone (PS), polyacrylonitrile (PAN), polyvinylidene difluoride (PVDF), regenerated cellulose, cellulose, cellulose ester, sulfonated polysulfone, sulfonated polyether sulfone, polyolefin, polyvinyl alcohol, polymethylmethacrylate, polyethylene tetrafluoride, and the like can be used. Because regenerated cellulose, cellulose, and cellulose ester are subjected to the breakdown by cellulase, ultrafiltration membranes with synthetic polymers such as PES or PVDF as a material are preferably used.

As a filtration method with ultrafiltration membrane, dead-end filtration and cross flow filtration are available with cross flow filtration being preferred from the viewpoint of inhibition of membrane fouling.

As for a membrane form of the ultrafiltration membrane, ones in an appropriate form such as a flat membrane type, a spiral type, a tubular type, or a hollow fiber type can be used. Specific examples thereof include G-5 type, G-10 type, G-20 type, G-50 type, PW type, and HWSUF type, which are available from DESAL; HFM-180, HFM-183, HFM-251, HFM-300, HFK-131, HFK-328, MPT-U20, MPS-U2OP, and MPS-U20S, available from KOCH; SPE1, SPE3, SPE5, SPE10, SPE30, SPV5, SPV50, and SOW30, available from Synder; ones corresponding to a molecular weight cut off of 3,000 to 10,000 in Microza (registered trademark) UF series which is manufactured by Asahi Kasei Corporation; and NTR7410 and NTR7450, manufactured by Nitto Denko Corporation.

Treatment with One or More Enzymes Selected from the Group Consisting of Pectinase, Glucoamylase, and Lipase We treat the cellulose-containing biomass with one or more enzymes selected from the group consisting of pectinase, glucoamylase, and lipase at a stage previous to step (1) or in step (1). The treatment of cellulose-containing biomass with one or more enzymes selected from the group consisting of pectinase, glucoamylase, and lipase at a stage previous to step (1) or in step (1) provides the effect of increasing the amount of the filamentous fungus-derived cellulase that can be recovered in the step (2), when compared to when such treatment is not carried out and, in particular, the effect of a remarkable increase in the amount of cellobiohydrolase to be recovered, the cellobiohydrolase being a major enzyme component in the hydrolysis of the cellulose-containing biomass, among the enzyme components contained in the filamentous fungus-derived cellulase.

Pectinase refers to an enzyme having the activity of breaking down pectin. Pectin is a complex polysaccharide constituting plants and containing as a major component a polygalacturonic acid including α-1,4-bonded galacturonic acids. The pectinase is defined as including enzyme species at least involved in the hydrolysis of pectin such as polygalacturonase (EC3.2.1.15), pectin lyase (EC4.2.2.10), pectate lyase (EC4.2.2.2), and pectate methyl esterase (EC3.1.1.11).

Glucoamylase (EC3.2.1.3) refers to an enzyme having the activity of hydrolyzing an α-1,4 bond at the non-reducing terminal end of starch.

Lipase refers to an enzyme that hydrolyzes lipids, in particular, an enzyme (EC3.1.1.3) having the activity of hydrolyzing ester bonds of fatty acids and triglycerides.

Pectinase, glucoamylase or lipase is preferably derived from the genus *Aspergillus*. Examples of the genus *Aspergillus* can include *Aspergillus nigar*, *Aspergillus orizae*, *Aspergillus awamori*, and *Aspergillus acretus*. The enzymes derived from the genus *Aspergillus* show the maximum enzymatic activity at an optimum reaction temperature of around 50° C., and can therefore be used at the same temperature when used in combination with the filamentous fungus-derived cellulase as will be described below.

The procedure that the cellulose-containing biomass is treated with one or more enzymes selected from the group consisting of pectinase, glucoamylase, and lipase at a stage previous to step (1) or in step (1) is specifically a step of hydrolyzing the cellulose-containing biomass in step (1) by one or more enzymes selected from the group consisting of pectinase, glucoamylase, and lipase before or during the hydrolysis by the filamentous fungus-derived cellulase in step (1). This procedure also includes a step of hydrolyzing the hydrolysate obtained in step (1) by one or more enzymes selected from the group consisting of pectinase, glucoamylase, and lipase. The cellulose-containing biomass in step (1) may be treated with one or more enzymes selected from the group consisting of pectinase, glucoamylase, and lipase alone or in combination before or during the hydrolysis with the cellulase in step (1); and the enzymatic treatment is preferably carried out at least during the hydrolysis with the cellulase in step (1).

The amount of the one or more enzymes selected from the group consisting of pectinase, glucoamylase, and lipase to be added at the stage previous to step (1) or in step (1) is not particularly restricted, and is preferably 1/10 or less in a weight ratio to the filamentous fungus-derived cellulase from the viewpoint of reducing the cost of enzyme. The amount of the enzymes to be added referred to herein is a total amount of the one or more enzymes selected from the group consisting of pectinase, glucoamylase, and lipase at the stage previous to step (1) or in step (1). The lower limit of the amount of the enzymes to be added is not particularly restricted as long as the desired effects are obtained, and is 0.001 mg/g of biomass in a weight ratio of the enzyme to be inputted to the weight of the cellulose-containing biomass.

The constitution of the one or more enzymes selected from the group consisting of pectinase, glucoamylase, and lipase to be added at the stage previous to step (1) or in step (1) may be pectinase, glucoamylase, and lipase, respectively, alone or a combination of two or more thereof. A combination of two or more of the enzymes is preferred; and a combination of the three enzymes is more preferred.

Other steps

Additionally, the hydrolysate obtained in step (1) is preferably subjected to solid-liquid separation. The solid-liquid separation is intended to separate the hydrolysate into a solution component (hereinafter referred to also as "aqueous sugar solution") containing sugars and a saccharification solid residue, thereby ensuring effective separation between and recovery of the sugar liquid and the filamentous fungus-derived cellulase in step (2).

A method for the solid-liquid separation is not particularly restricted; and the hydrolysate can be subjected to solid-liquid separation by centrifugation with a screw decanter or by press filtration with a filter press or a belt press. Press filtration with a filter press or a belt press is preferred, and provides a solution component containing less insoluble solids and less turbid substances, when compared to centrifugation. Less turbid substances are also preferred from the viewpoint of inhibiting the fouling of the ultrafiltration membrane at a later stage. When the solid-liquid separation is carried out through press filtration by a filter press or a belt press, a period of time for the solid-liquid separation treatment can be effectively reduced by the treatment with one or more enzymes selected from the group consisting of pectinase, glucoamylase, and lipase at the stage previous to step (1) or in step (1).

The aqueous sugar solution obtained by the solid-liquid separation is preferably filtered through a microfiltration membrane before being subjected to step (2). Since the filtration through a microfiltration membrane allows removal of solid contents which could not completely be separated by the solid-liquid separation, step (2) can be carried out more efficiently.

The microfiltration membrane is a membrane having an average fine pore diameter of 0.01 µm to 5 mm. The material of the microfiltration membrane is not particularly restricted as long as it can remove solid contents which could not completely be separated by the above-mentioned solid-liquid separation; and examples thereof include organic materials such as cellulose, cellulose ester, polysulfone, polyether sulfone, chlorinated polyethylene, polypropylene, polyolefin, polyvinyl alcohol, polymethylmethacrylate, polyvinylidene fluoride, and polyethylene tetrafluoride; metals such as stainless; and inorganic materials such as ceramic.

The obtained sugar liquid is usable as a fermentation raw material; and chemical substances can be produced by culturing microorganisms. Specific examples of the chemical substance can include substances mass-produced in the fermentation industry such as alcohols, organic acids, amino acids, and nucleic acids. For example, there can be listed alcohols such as ethanol, 1,3-propanediol, 1,4-butanediol, or glycerol; organic acids such as acetic acid, lactic acid, pyruvic acid, succinic acid, malic acid, itaconic acid, or citric acid; nucleosides such as inosine or guanosine; nucleotides such as inosinic acid or guanylic acid; and amine compounds such as cadaverine. Further, the sugar liquid can be applied to production of enzymes, antibiotics, recombinant proteins or the like.

EXAMPLES

By way of examples, our methods will be specifically described below. This disclosure is, however, not limited to the examples.

Reference Example 1

Method of Preparing Filamentous Fungus-Derived Cellulase (Culture Liquid)

A filamentous fungus-derived cellulase (culture liquid) was prepared by the following method.

Preculture

5% (w/vol) of corn steep liquor, 2% (w/vol) of glucose, 0.37% (w/vol) of ammonium tartrate, 0.14% (w/vol) of ammonium sulfate, 0.2% (w/vol) of potassium dihydrogen phosphate, 0.03% (w/vol) of calcium chloride dihydrate, 0.03% (w/vol) of magnesium sulfate heptahydrate, 0.02% (w/vol) of zinc chloride, 0.01% (w/vol) of iron (III) chloride hexahydrate, 0.004% (w/vol) of copper (II) sulfate pentahydrate, 0.0008% (w/vol) of manganese chloride tetrahydrate, 0.0006% (w/vol) of boric acid, and 0.0026% (w/vol) of hexaammonium heptamolybdate tetrahydrate were added to distilled water; and 100 mL of the solution was charged into a 500-mL Erlenmeyer flask with a baffle and subjected to autoclave sterilization at a temperature of 121° C. for 15 minutes. After the solution was allowed to cool, PE-M and Tween 80, each which had been autoclave-sterilized at a temperature of 121° C. for 15 minutes separately from this, were added in an amount of 0.01% (w/vol) each. *Trichoderma reesei* ATCC66589 was planted at $1 \times 10^5$ fungi/mL into this preculture medium, and shake-cultured at a temperature of 28° C. and 180 rpm for 72 hours to prepare a preculture (shaker: BIO-SHAKER BR-40LF manufactured by TAITEC).

Main Culture

5% (w/vol) of corn steep liquor, 2% (w/vol) of glucose, 10% (w/vol) of cellulose (Avicel), 0.37% (w/vol) of ammonium tartrate, 0.14% (w/vol) of ammonium sulfate, 0.2% (w/vol) of potassium dihydrogen phosphate, 0.03% (w/vol) of calcium chloride dihydrate, 0.03% (w/vol) of magnesium sulfate heptahydrate, 0.02% (w/vol) of zinc chloride, 0.01% (w/vol) of iron (III) chloride hexahydrate, 0.004% (w/vol) of copper (II) sulfate pentahydrate, 0.0008% (w/vol) of manganese chloride tetrahydrate, 0.0006% (w/vol) of boric acid, and 0.0026% (w/vol) of hexaammonium heptamolybdate tetrahydrate were added to distilled water; and 2.5 L of the solution was charged into a 5-L volume stirring jar (DPC-2A manufactured by ABLE) and subjected to autoclave sterilization at a temperature of 121° C. for 15 minutes. After the solution was allowed to cool, PE-M and Tween 80, each which had been autoclave-sterilized at a temperature of 121° C. for 15 minutes separately from this, were each added in an amount of 0.1%. 250 mL of *Trichoderma reesei* ATCC66589, which had been precultured in the liquid medium by the above-mentioned method, was inoculated, and then shake-cultured under the conditions: a temperature of 28° C.; 87 hours; 300 rpm; and an amount of aeration: 1 vvm. After centrifugation, a supernatant was subjected to membrane filtration (Stericup-GV manufactured by Millipore Corporation; material: PVDF). The culture liquid controlled under the conditions described above was used as a filamentous fungus-derived cellulase in the following Examples.

Reference Example 2

Measurement of Concentration of Sugars

The concentration of glucose and xylose that were contained in a sugar liquid was quantified under HPLC conditions described below by comparing to a standard sample:
Column: Luna NH$_2$ (manufactured by Phenomenex)
Mobile phase: Milli-Q: acetonitrile=25:75 (flow rate 0.6 mL/min)
Reaction solution: none
Detection method: RI (differential refractive index)
Temperature: 30° C.

Reference Example 3

Method of Measuring Activities of Filamentous Fungus-Derived Cellulase

As for cellulase activities, determined were the activities of cellobiohydrolase and endoglucanase involved in the breakdown of cellulose from the activity of breaking down (1) 4-nitrophenyl-β-D-lactopyranoside (pNP-Lac); the activity of β-glucosidase from the activity of breaking down (2) 4-nitrophenyl-β-D-glucopyranoside (pNP-Glc); and the activities of endoxylanase and xylosidase involved in the breakdown of xylan as a major component of hemicellulose from the activity of breaking down (3) 4-nitrophenyl-β-D-xylopyranoside (pNP-Xyl). The above (1) to (3) substrates are collectively refers to pNP-sugars.

To 0.9 mL of 100 mM acetic acid buffer (pH 5.0) containing each substrate at a concentration of 1 mM each, 0.1 mL of enzyme liquid was added and allowed to react at 30° C. The reaction time was set to 60 minutes when the substrate was pNP-Lac, 10 minutes for pNP-Glc, and 30 minutes for pNP-Xyl. After the reaction, 0.1 mL of 2 M aqueous sodium carbonate solution was added to terminate the reaction and the absorbance at 405 nm was measured (ODtest). The absorbance at 405 nm was also measured in the same manner as described above for, as a blank, one prepared by adding, in the order mentioned, 2 M aqueous sodium carbonate solution and the enzyme liquid to the substrate solution (ODblank). The amount of enzyme that generates 1 μmol of 4-nitrophenol for one minute is defined as 1 U in the above reaction system, and an activity value (U/mL) was calculated according to the following formula. The millimolar molecular extinction coefficient of 4-nitrophenol in the above reaction system is 17.2 L/mmol/cm.

The activity of breaking down pNP-Lac (U/mL)={(ODtest−ODblank)×1.1 (mL)×enzyme dilution ratio}/{17.2×60 (minutes)×0.1 (mL)}

The activity of breaking down pNP-Glc (U/mL)={(ODtest−ODblank)×1.1 (mL)×enzyme dilution ratio}/{17.2×10 (minutes)×0.1 (mL)}

The activity of breaking down pNP-Xyl (U/mL)={(ODtest−ODblank)×1.1 (mL)×enzyme dilution ratio}/{17.2×30 (minutes)×0.1 (mL)}

Example 1

As cellulose-containing biomass, (1) a corn hull, (2) a soybean hull, (3) straw, and (4) bagasse were used. Pretreatment of the cellulose-containing biomass prior to the hydrolysis by the filamentous fungus-derived cellulase was carried out under pretreatment conditions that were different depending on raw material as follows.

(1) Corn Hull (Pretreatment Condition: Dilute Sulfuric Acid Treatment)

A dried corn hull product made in China was used (purchased from GODO Co., Ltd.). 2.3 kg of 13 g/L sulfuric acid water was added to 1 kg of a corn hull (dried) so that the water content arrived at 70% (30 mg of sulfuric acid/g of corn hull). The corn hull with sulfuric acid water being added was subjected to a hydrothermal treatment using an autoclave at 120° C. for 30 minutes. After autoclaving, ammonia water was added to the pretreatment product to adjust its pH to 5. This product was defined as a pretreatment product 1.

(2) Soybean Hull (Pretreatment Condition: Dilute Sulfuric Acid Treatment)

A dried soybean hull product made in China was used (purchased from GODO Co., Ltd.). 2.3 kg of 65 g/L sulfuric acid water was added to 1 kg of a soybean hull (dried) so that the water content arrived at 70% (150 mg of sulfuric acid/g of soybean hull). The soybean hull with sulfuric acid water being added was subjected to a hydrothermal treatment using an autoclave at 120° C. for 30 minutes. After autoclaving, ammonia water was added to the pretreatment product to adjust its pH to 5. This product was defined as a pretreatment product 2.

($^3$) Straw (Pretreatment Condition: Hydrothermal Treatment)

A dried straw (rice straw) product made in Japan was used (offered from a farmer). Straw was ground in a rotary cutter mill RCM-400 (8-mm mesh) manufactured by NARA MACHINERY CO., LTD. at a rotation speed of 420 rpm, and then subjected to a hydrothermal treatment. A blasting apparatus (reactor 2-L size) manufactured by Nihon Dennetsu Co., Ltd. was used. As a steam generator, an electric boiler of 40 kW was used. Since the treatment temperature is unambiguously determined when the treatment pressure is set, the treatment was carried out under the reaction conditions: 215° C. and 5 minutes. Under these conditions, 200 g of the ground straw was inputted each time, in a total of five times. The blasted water-containing solid content was stirred while 2 L of water was added thereto, and separated into a hydrothermally-treated liquid and solid matter by using a centrifuge for laboratory use "HimacCF7D2" manufactured by Hitachi Koki Co., Ltd. at 5000 rpm. The water content of the solid matter was adjusted to 70%, and ammonia water was used to adjust the pH to 5. This product was defined as a pretreatment product 3.

(4) Bagasse (Pretreatment Condition: Dilute Sulfuric Acid Treatment)

A dried bagasse product made in Taiwan was used (purchased from Taito-nosan). Bagasse was ground in a rotary cutter mill RCM-400 (20-mm mesh) manufactured by NARA MACHINERY CO., LTD. at a rotation speed of 420 rpm. 2.3 kg of 13 g/L sulfuric acid water was added to 1 kg of bagasse (dried) so that the water content arrived at 70% (30 mg of sulfuric acid/g of bagasse). The bagasse with sulfuric acid water being added was subjected to a hydrothermal treatment using an autoclave at 120° C. for 30 minutes. After autoclaving, ammonia water was added to the pretreatment product to adjust its pH to 5. This product was defined as a pretreatment product 4.

To the pretreatment products 1 to 4, water was added to attain a solid content concentration of 10%. Further, the filamentous fungus-derived cellulase, which had been prepared in Reference Example 1, was added for hydrolysis. The amount of the filamentous fungus-derived cellulase added was: 2 mg/g of pretreatment product 1; 4 mg/g of pretreatment product 2; 8 mg/g of pretreatment product 3; and 8 mg/g of pretreatment product 4, and then hydrolysis was started. A hydrolysis reaction was carried out at 50° C. for 48 hours.

In the hydrolysis in step (1), pectinase ("Pectinase PL Amano" manufactured by Amano Enzyme Inc.), glucoamylase ("AMYLOGLUCOSIDASE" manufactured by Megazyme), and lipase ("Lipase AS Amano" manufactured by Amano Enzyme Inc.) were added in each combination indicated in Table 1 (the amount of the enzyme(s) added was: 0.2 mg/g of pretreatment product when one of the enzymes was added; 0.1 mg/g of pretreatment product each when two of the enzymes were added in combination; 0.06 mg/g of pretreatment product each when the three enzymes were added in combination) for enzymatic treatment. When none of pectinase, Glucoamylase and lipase was added was defined as Comparative Example 1.

8 kg of the respective enzymatically-treated materials obtained in the above step were pressed into a filter press manufactured by Yabuta Kikai Co., Ltd. at 0.2 MPa for solid-liquid separation. A woven fabric T2731C (made of polyester, double cloth) manufactured by Yabuta Kikai Co., Ltd. was used as a filter cloth. Pneumatic pressing was conducted at a pressure of 0.3 MPa; and a pressed liquid was recovered from the biomass subjected to the solid-liquid separation. This liquid was mixed with the liquid separated by the solid-liquid separation and 6 kg of an aqueous sugar solution was recovered as a solution component. Table 1 indicates a period of time required for the solid-liquid separation.

TABLE 1

Period of time required to complete solid-liquid separation of 8 kg sugar liquid by filter press

|  | Corn hull-derived hydrolysate | Soybean hull-derived hydrolysate | Straw (rice)-derived hydrolysate | Bagasse-derived hydrolysate |
|---|---|---|---|---|
| Comparative Example 1 | 280 min | 50 min | 44 min | 45 min |
| Pectinase | 204 min | 40 min | 31 min | 40 min |
| Glucoamylase | 260 min | 45 min | 42 min | 40 min |
| Lipase | 255 min | 48 min | 43 min | 36 min |
| Pectinase + glucoamylase | 142 min | 33 min | 27 | 38 min |
| Glucoamylase + lipase | 233 min | 43 min | 40 | 32 min |
| Pectinase + lipase | 150 min | 34 min | 26 | 32 min |
| Pectinase + lipase + glucoamylase | 118 min | 25 min | 22 min | 25 min |

After filtration of the whole amount of 6 kg of the respective recovered aqueous sugar solutions through a microfiltration membrane having a pore diameter of 0.22 μm, the obtained permeate was further filtered through an ultrafiltration membrane. As the ultrafiltration membrane, HFU (manufactured by Toray Membrane USA; material: polyvinylidene fluoride; molecular weight cut off: 150,000) was used. Ultrafiltration was carried out by using a flat membrane filtration unit "SEPA-II" (manufactured by GE Osmonics) under the conditions: a membrane surface linear speed of 20 cm/sec and a filtration pressure of 3 MPa, until the amount of the liquid recovered from the non-permeation side reached 0.6 L. The enzyme(s) in the non-permeate obtained after the ultrafiltration treatment was defined as recovered enzyme(s), and the activities of the recovered enzyme(s) were measured by the method of measuring the activities of filamentous fungus-derived cellulase in Reference Example 3. Tables 2 to 5 indicate the activities of the recovered enzyme(s) relative to the inputted filamentous fungus-derived cellulase.

TABLE 2

Activities of enzyme(s) recovered from corn hull-derived hydrolysate

|  | pNP-Lac breakdown activity | pNP-Glc breakdown activity | pNP-Xyl breakdown activity |
|---|---|---|---|
| Filamentous fungus-derived cellulase | 100% | 100% | 100% |
| Comparative Example 1 | 15% | 17% | 25% |
| Pectinase | 30% | 17% | 28% |
| Glucoamylase | 23% | 25% | 30% |
| Lipase | 25% | 20% | 40% |
| Pectinase + glucoamylase | 45% | 35% | 40% |
| Glucoamylase + lipase | 55% | 77% | 55% |
| Pectinase + lipase | 75% | 60% | 50% |
| Pectinase + lipase + glucoamylase | 95% | 90% | 85% |

TABLE 3

Activities of enzyme(s) recovered from soybean hull-derived hydrolysate

|  | pNP-Lac breakdown activity | pNP-Glc breakdown activity | pNP-Xyl breakdown activity |
|---|---|---|---|
| Filamentous fungus-derived cellulase | 100% | 100% | 100% |
| Comparative Example 1 | 10 | 15 | 40 |
| Pectinase | 30 | 25 | 40 |
| Glucoamylase | 20 | 20 | 45 |
| Lipase | 25 | 20 | 40 |
| Pectinase + glucoamylase | 60 | 35 | 55 |
| Glucoamylase + lipase | 60 | 60 | 55 |
| Pectinase + lipase | 65 | 50 | 60 |
| Pectinase + lipase + glucoamylase | 80 | 75 | 75 |

TABLE 4

Activities of enzyme(s) recovered from straw (rice)-derived hydrolysate

|  | pNP-Lac breakdo activity | pNP-Glc breakdown activity | pNP-Xyl breakdn activity |
|---|---|---|---|
| Filamentous fungus-derived cellulase | 100% | 100% | 100% |
| Comparative Example 1 | 35 | 55 | 50 |
| Pectinase | 45 | 55 | 60 |
| Glucoamylase | 50 | 55 | 50 |
| Lipase | 45 | 60 | 55 |
| Pectinase + glucoamylase | 67 | 70 | 75 |
| Glucoamylase + lipase | 70 | 65 | 80 |
| Pectinase + lipase | 65 | 80 | 70 |
| Pectinase + lipase + glucoamylase | 95 | 95 | 95 |

TABLE 5

Activities of enzyme(s) recovered from bagasse-derived hydrolysate

|  | pNP-Lac breakdown activity | pNP-Glc breakdown activity | pNP-Xyl breakdown activity |
|---|---|---|---|
| Filamentous fungus-derived cellulase | 100% | 100% | 100% |
| Comparative Example 1 | 25 | 50 | 50 |
| Pectinase | 50 | 60 | 60 |
| Glucoamylase | 30 | 60 | 60 |
| Lipase | 30 | 60 | 60 |
| Pectinase + glucoamylase | 60 | 70 | 70 |
| Glucoamylase + lipase | 50 | 65 | 70 |
| Pectinase + lipase | 70 | 70 | 70 |

TABLE 5-continued

Activities of enzyme(s) recovered from bagasse-derived hydrolysate

|  | pNP-Lac breakdown activity | pNP-Glc breakdown activity | pNP-Xyl breakdown activity |
|---|---|---|---|
| Pectinase + lipase + glucoamylase | 90 | 80 | 80 |

INDUSTRIAL APPLICABILITY

The method of producing a sugar liquid involves the use of cellulose-containing biomass as a raw material, and the obtained sugar liquid can be used as a fermentation raw material for various chemical substances.

The invention claimed is:

1. A method of producing a sugar liquid from cellulose-containing biomass, comprising:
   step (1) of hydrolyzing the cellulose-containing biomass with a cellulase selected from the group consisting of a cellulase derived from a filamentous fungus, a cellulase derived from the genus *Cellulomonas*, a cellulase derived from the genus *Chlostridium* and a cellulase derived from the genus *Streptomyces*;
   step (2) of filtering a hydrolysate obtained in step (1) through an ultrafiltration membrane to recover the cellulase as a non-permeate and obtain a sugar liquid as a permeate; and
   a step (3) of recycling enzymes recovered in the non-permeate in step (2) for use in step (1);
   wherein the cellulose-containing biomass is treated with lipase, pectinase, and glucoamylase in step (1).

2. The method according to claim 1, wherein said cellulose-containing biomass is one or more biomasses selected from the group consisting of grain hull biomass, straw, and bagasse.

3. The method according to claim 2, wherein said grain hull biomass is one or more biomasses selected from the group consisting of corn hull, soybean hull, and wheat hull.

4. The method according to claim 1, wherein the weight of one or more enzymes selected from the group consisting of said lipase, pectinase, and glucoamylase is 1/10 or less based on the weight of the cellulase.

5. A method of producing a sugar liquid from cellulose-containing biomass, comprising:
   step (1) of hydrolyzing the cellulose-containing biomass with a cellulase selected from the group consisting of a cellulase derived from a filamentous fungus, a cellulase derived from the genus *Cellulomonas*, a cellulase derived from the genus *Chlostridium* and a cellulase derived from the genus *Streptomyces*, and increasing in an amount of recoverable cellulase in a hydrolysate by treating the cellulose-containing biomass with lipase, pectinase, and glucoamylase; and
   step (2) of filtering the hydrolysate obtained in step (1) through an ultrafiltration membrane to recover the cellulase as a non-permeate and obtain a sugar liquid as a permeate.

* * * * *